United States Patent [19]

Nelson

[11] Patent Number: 4,559,826

[45] Date of Patent: Dec. 24, 1985

[54] PRECISION SOURCE OF ACOUSTIC RADIATION

[75] Inventor: Craig E. Nelson, Seattle, Wash.

[73] Assignee: TAB Leasing, Seattle, Wash.

[21] Appl. No.: 650,806

[22] Filed: Sep. 14, 1984

[51] Int. Cl.$^4$ ............................................ G01N 29/00
[52] U.S. Cl. .................................... 73/632; 73/1 DV;
73/646; 367/13; 310/317
[58] Field of Search ................ 367/13, 137; 73/1 DV,
73/632, 646; 310/316, 317; 128/660

[56] References Cited

U.S. PATENT DOCUMENTS

| | | |
|---|---|---|
| 3,351,902 | 11/1967 | Padberg, Jr. . |
| 3,407,649 | 10/1968 | Dickinson, III . |
| 3,544,866 | 12/1970 | McLeroy . |
| 3,573,781 | 4/1971 | Shoh .................................... 310/317 |
| 3,774,167 | 11/1973 | Puckette et al. . |
| 4,277,710 | 7/1981 | Harwood et al. ................... 310/316 |
| 4,311,922 | 1/1982 | Puckette . |
| 4,319,155 | 3/1982 | Nakai et al. ......................... 310/317 |

OTHER PUBLICATIONS

"Tone Burst Testing of Pulse-Echo Transducers", Erikson, *IEEE Transactions on Sonics & Ultrasonics*, vol. SU-26, No. 1, Jan. 1979, pp. 7-14.

*Primary Examiner*—Howard A. Birmiel
*Attorney, Agent, or Firm*—Christensen, O'Connor, Johnson & Kindness

[57] ABSTRACT

A precision acoustic source that is capable of producing acoustic radiation having peak and average power levels that are independently and simultaneously adjustable. The apparatus comprises an acoustic transducer and drive means for producing a drive signal comprising a series of drive pulses to the transducer, such that the transducer produces acoustic radiation having selected peak and average power levels. The drive means comprises means for establishing a series of fixed-length clock cycles, means for generating a series of trigger signals, pulse generating means responsive to each trigger signal to produce a selected number of standard pulses, an amplifier for generating a drive pulse in response to each standard pulse. The amplifier adjusts the amplitude of each drive pulse such that the peak power of the acoustic radiation is equal to the selected peak power level. Each trigger signal occurs either R or S clock cycles after the preceding trigger signal, R and S being positive integers. The apparatus further comprises means for determining R and S such that the average power of the acoustic radiation is equal to the selected average power level at the selected peak power level. In a preferred embodiment, the number S is equal to R+1.

9 Claims, 4 Drawing Figures

PRECISION SOURCE OF ACOUSTIC RADIATION

FIELD OF THE INVENTION

The present invention relates to a source of acoustic radiation and, in particular, to an apparatus for generating acoustic radiation of preselected peak and average power levels.

BACKGROUND OF THE INVENTION

The increased medical use of ultrasound has led to an increased need for devices that can accurately measure the power output of instruments that generate acoustic radiation. Hydrophones and other devices for measuring acoustic power have been available for many years. However to assure accuracy, a power measuring device must be periodically calibrated by determining the response of the device to acoustic radiation of known power. In the past, the calibration of acoustic power measuring devices has been difficult due to the lack of an acoustic source capable of producing acoustic radiation having precise and adjustable peak and average power levels. As a result, most workers in the field have either built nonadjustable power sources for making simple measurements or have used a troublesome reciprocity method to calibrate their sources.

SUMMARY OF THE INVENTION

The present invention provides a precision acoustic source that is capable of producing acoustic radiation having peak and average power levels that are independently and simultaneously adjustable over a wide range of values of each parameter. The apparatus of the present invention can be calibrated against a standard acoustic power measuring device at any convenient peak and average power level to a known degree of accuracy. The apparatus will then generate all other selectable power levels to the same degree of accuracy, and may therefore be used to calibrate other power measuring devices over a wide range of power levels.

In one preferred embodiment, the invention comprises an acoustic transducer and drive means for producing a drive signal to the acoustic transducer, such that the transducer produces acoustic radiation having selected peak and average power levels. The drive signal comprises a series of drive pulses. The drive means comprises means for establishing a series of fixed length clock cycles, means for generating a series of trigger signals, pulse generating means responsive to each trigger signal to produce a selected number of standard pulses, and amplifier means for generating a drive pulse in response to each standard pulse. The amplifier means adjusts the amplitude of each drive pulse such that the peak power of the acoustic radiation is equal to the selected peak power level. Each trigger signal occurs either R or S clock cycles after the preceding trigger signal, R and S being positive integers. The apparatus further comprises means for determining R and S such that the average power of the acoustic radiation is equal to the selected average power level at the selected peak power level.

In a further aspect of the invention, the means for generating a series of trigger signals comprises counting means and selection means. The counting means generates a first timing signal R clock cycles after the preceding trigger signal, and generates a second timing signal S clock cycles after the preceding trigger signal. The selection means selects either the first or second timing signal, and produces the next trigger signal in response to the selected timing signal. In a preferred embodiment, the number S is equal to R+1.

DETAILED DESCRIPTION OF THE INVENTION

Figure 1:
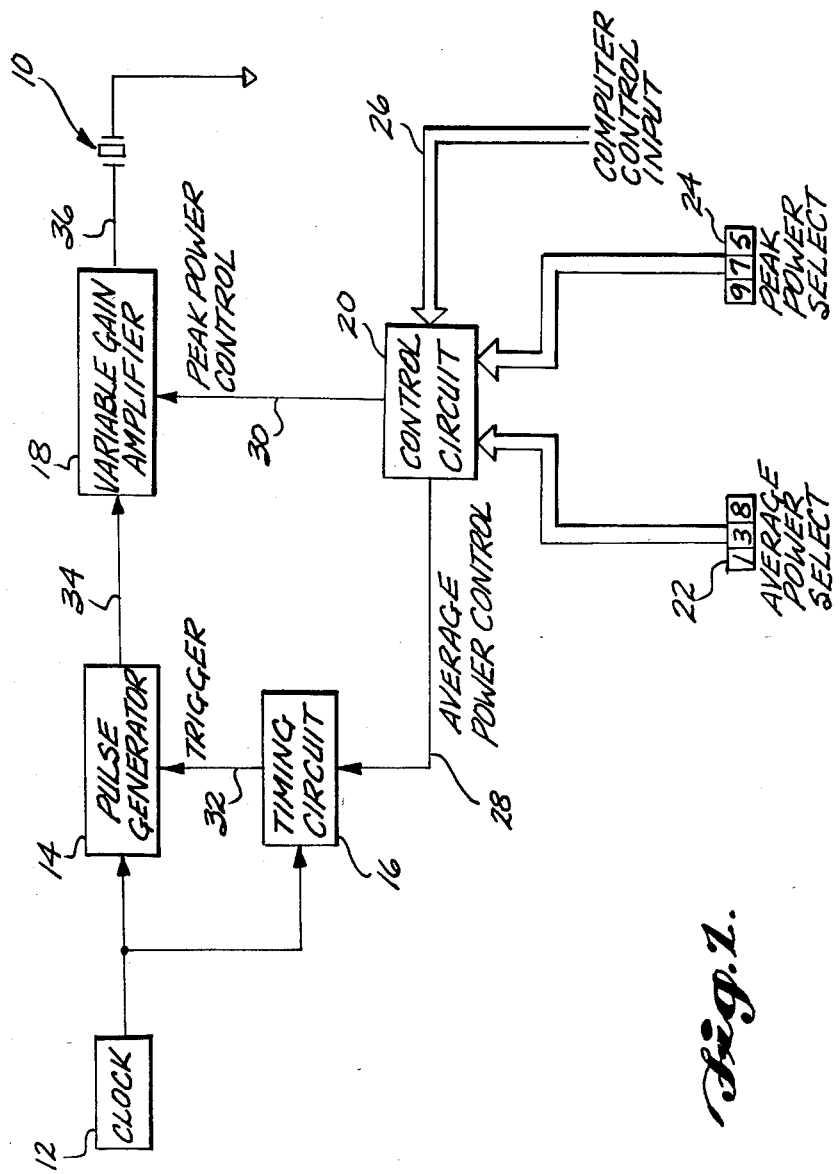
FIG. 1 is a block diagram of one preferred embodiment of the acoustic source of the present invention.

One preferred embodiment of the present invention is illustrated in block diagram form in FIG. 1. The apparatus comprises acoustic transducer 10, clock 12, pulse generator 14, timing circuit 16, variable gain amplifier 18 and control circuit 20. Control circuit 20 receives signals representing user selected levels for the average and peak power of the acoustic radiation. Such signals may be provided via manually operated switches 22 and 24, or may be provided by a computer control device (not illustrated) via data path 26. In either case, control circuit 20 responds by generating an AVERAGE POWER CONTROL signal on line 28 and a PEAK POWER CONTROL signal on line 30. The AVERAGE POWER CONTROL signal is received by timing circuit 16, and the timing circuit responds by issuing a series of trigger signals on line 32. Each trigger signal causes pulse generator 14 to produce a predetermined number of standard pulses on line 34. The standard pulses are amplified by variable gain amplifier 18 to produce a drive signal consisting of a series of drive pulses on line 36. The degree of amplification provided by the variable gain amplifier is controlled by the PEAK POWER CONTROL signal on line 30.

Figure 2:
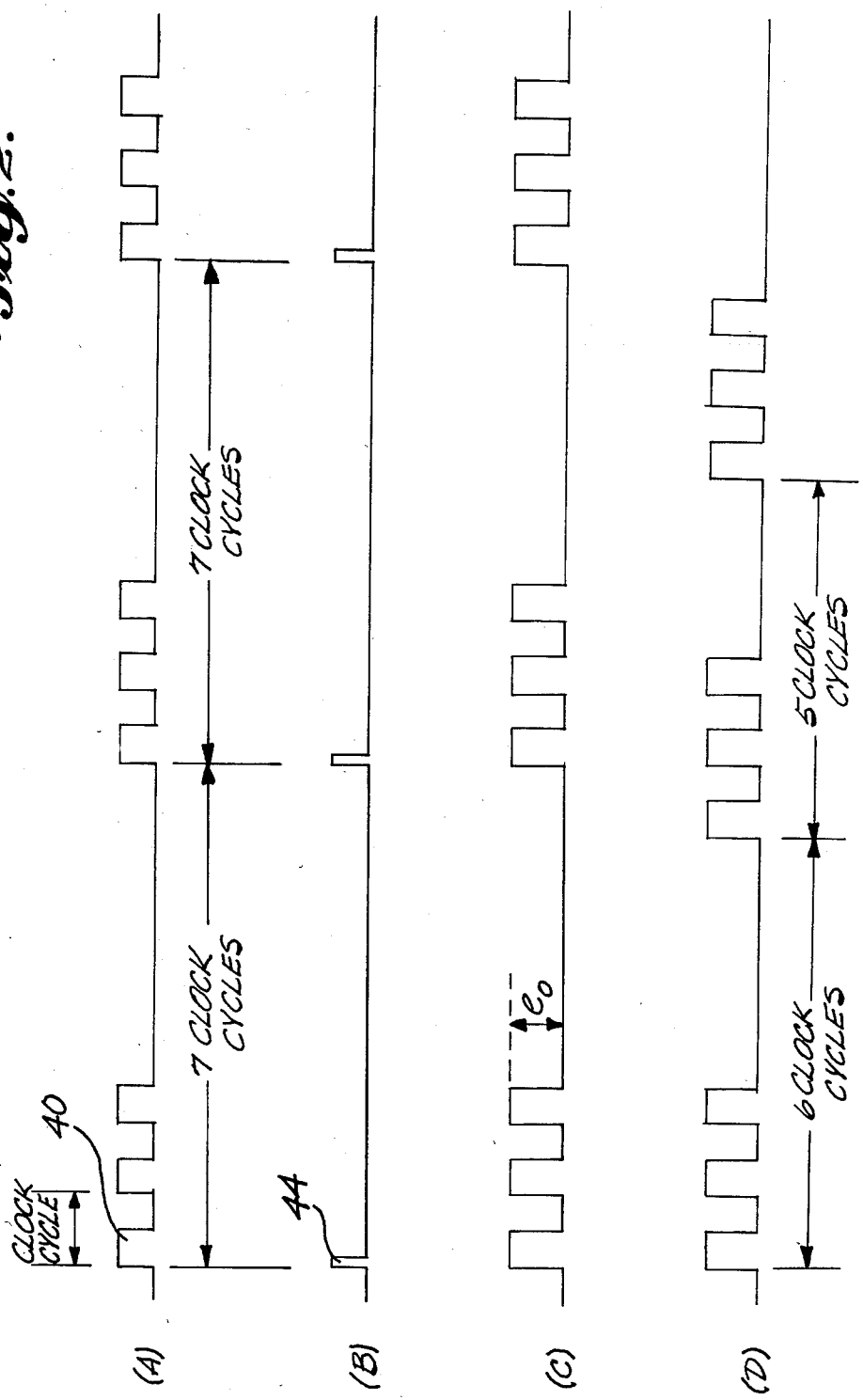
FIG. 2 is a signal and timing diagram illustrating the generation of drive pulses in the apparatus of FIG. 1.

FIG. 2 illustrates a preferred method by which the peak and average power of the acoustic radiation is controlled in accordance with the present invention. FIG. 2A shows one example of a drive signal produced by variable gain amplifier 18. The drive signal comprises a series of drive pulses 40, the drive pulses occurring in groups of three drive pulses separated by periods of time during which no drive pulse occur. All drive pulses have the same duration. The full cycle period of a single drive pulse 40 is defined as one clock cycle, and in the illustrated example the groups of drive pulses recur at intervals of seven clock cycles. FIG. 2B illustrates the trigger signal on line 32 corresponding to the drive pulses of FIG. 2A. The trigger signal comprises a series of trigger pulses 44, the trigger pulses also recurring at intervals of seven clock cycles. Each trigger pulse 44 causes pulse generator 14 to produce three standard pulses on line 34, which standard pulses are amplified by variable gain amplifier 18 to produce drive pulses 40 of FIG. 2A.

FIG. 2C schematically illustrates the method by which the peak power of the acoustic radiation is controlled. As previously described, control circuit 20 responds to the selected peak power level by sending an appropriate PEAK POWER CONTROL signal to variable gain amplifier 18 over line 30. The variable gain amplifier in turn adjusts the height (voltage) $e_o$ of the drive pulses to produce a drive signal having the selected peak power level. Preferably, the PEAK POWER CONTROL signal is a digital signal, and the variable gain amplifier produces drive pulses that have a height $e_o$ that is a linear function of the magnitude of the PEAK POWER CONTROL signal. If $e_i$ represents the magnitude of the standard pulses input to the variable gain amplifier, then:

$$e_o = K_a \cdot e_i \tag{1}$$

where $K_a$ is the gain provided by the variable gain amplifier. If the efficiency of transducer 10 is $K_x$ watts per volts squared, then the power output by the transducer, $P_o$, can be written as:

$$P_o = K_x \cdot K_a^2 \cdot e_i^2 \tag{2}$$

Solving for $K_a$ gives:

$$K_a = \frac{1}{e_i} \sqrt{\frac{P_o}{K_x}} \tag{3}$$

Since there may be a soft saturation form of nonlinearity in the transducer or in the variable gain amplifier, it is desirable to modify equation (3) by substituting a polynomial in $P_o$ in place of $P_o$. For example, to include a quadratic correction, equation (3) would become:

$$K_a = \frac{1}{e_i} \sqrt{\frac{P_o + K_s \cdot P_o^2}{K_x}} \tag{4}$$

Thus, after the parameters $K_s$ and $K_x$ are established by calibration procedures, control circuit 20 can establish the gain $K_a$ to be produced by the variable gain amplifier once the required peak power $P_o$ is specified. The gain $K_a$ can then be converted into a PEAK POWER CONTROL signal of appropriate magnitude.

Once control circuit 20 has established a suitable gain $K_a$ to satisfy the selected peak power constraint, it then determines the rate at which drive pulses are sent to the transducer in order to satisfy the average power constraint. The ratio of average power to peak power may be expressed as a duty cycle, D, which may be written as:

$$D = \frac{\text{average power}}{\text{peak power}} = \tag{5}$$

$$\frac{(\text{energy per pulse}) - (\text{pulses per second})}{\text{peak power}}$$

The apparatus of FIG. 1 produces individual drive pulses 40 whose energy content is constant for a given amplifier gain $K_a$, and controls the average power and the duty cycle D by adjusting the fraction of clock cycles that contain drive pulses, i.e., by adjusting the pulses per second.

In the embodiment illustrated in FIG. 2, pulse generator 14 is adapted to produce three standard pulses in response to each trigger pulse. Each group of three standard pulses in turn results in a corresponding group of three drive pulses. In the example of FIG. 2A, each group of three drive pulses is followed by an "off time" of four clock cycles during which no drive pulses occur, to produce a total "wait time" of seven clock cycles between the start of successive drive pulse groups. The drive signal of FIG. 2A therefore corresponds to a duty cycle of 3/7. To produce the drive signal of FIG. 2A, timing circuit 16 could issue a trigger pulse 44 every seven clock cycles. This simple approach, however, is capable of producing only a limited number of duty cycles. For example, to produce a duty cycle of 0.55 (6/11), it would be necessary to follow each group of three drive pulses by an off time of 2.5 clock cycles by using a wait time of 5.5 clock cycles. Unfortunately, the use of partial cycles in the drive signal would result in difficult to correct irregularities in the output acoustic wave pulses. To overcome this difficulty, the present invention provides for two wait times, each comprising an integer number of clock cycles, and controls the relative frequency of the two wait times to produce the desired duty cycle and average power. FIG. 2D provides a simple example of this technique. In FIG. 2D a first wait time of six clock cycles is followed by a second wait time of five clock cycles. By alternating the first and second wait times such that each wait time is used at a frequency of 50%, the required duty cycle of 6/11 is achieved. By varying the frequency of use of the five and six clock cycle wait times, all duty cycles between 3/6 and 3/5 can be achieved. By appropriately selecting the two wait times and the frequency of their use, any duty cycle can be achieved to any degree of accuracy required.

If W is defined to be the average wait time between the beginning of successive drive pulse groups, i.e., the time between successive trigger pulses, and if Q is the number of drive pulses in each group, then the duty cycle D may be written as:

$$D = Q/W \tag{6}$$

If R and S are the number of clock cycles in the first and second wait times respectively, and if M is the frequency at which the first wait time R is used divided by the frequency at which the second wait time S is used, then equation (6) can be rewritten as:

$$D = \frac{Q \cdot (M + 1)}{R \cdot M + S} \tag{7}$$

Equation (7) may be solved for M as follows:

$$M = \frac{Q - D \cdot S}{D \cdot R - Q} \tag{8}$$

Thus for any desired values for Q, R and S, the relative frequency M can be calculated to produce any selected duty cycle and therefore any average power level up to the peak power level.

The special case of $S = R + 1$ may be formulated by setting S equal to $R + 1$ in the above equations. However a more direct and easy to implement approach for this special case is to simply rewrite equation (6) as:

$$W = \frac{Q}{D} = \text{Int}\left[\frac{W}{D}\right] + \text{Fr}\left[\frac{W}{D}\right] = R + F \tag{9}$$

Figure 3:
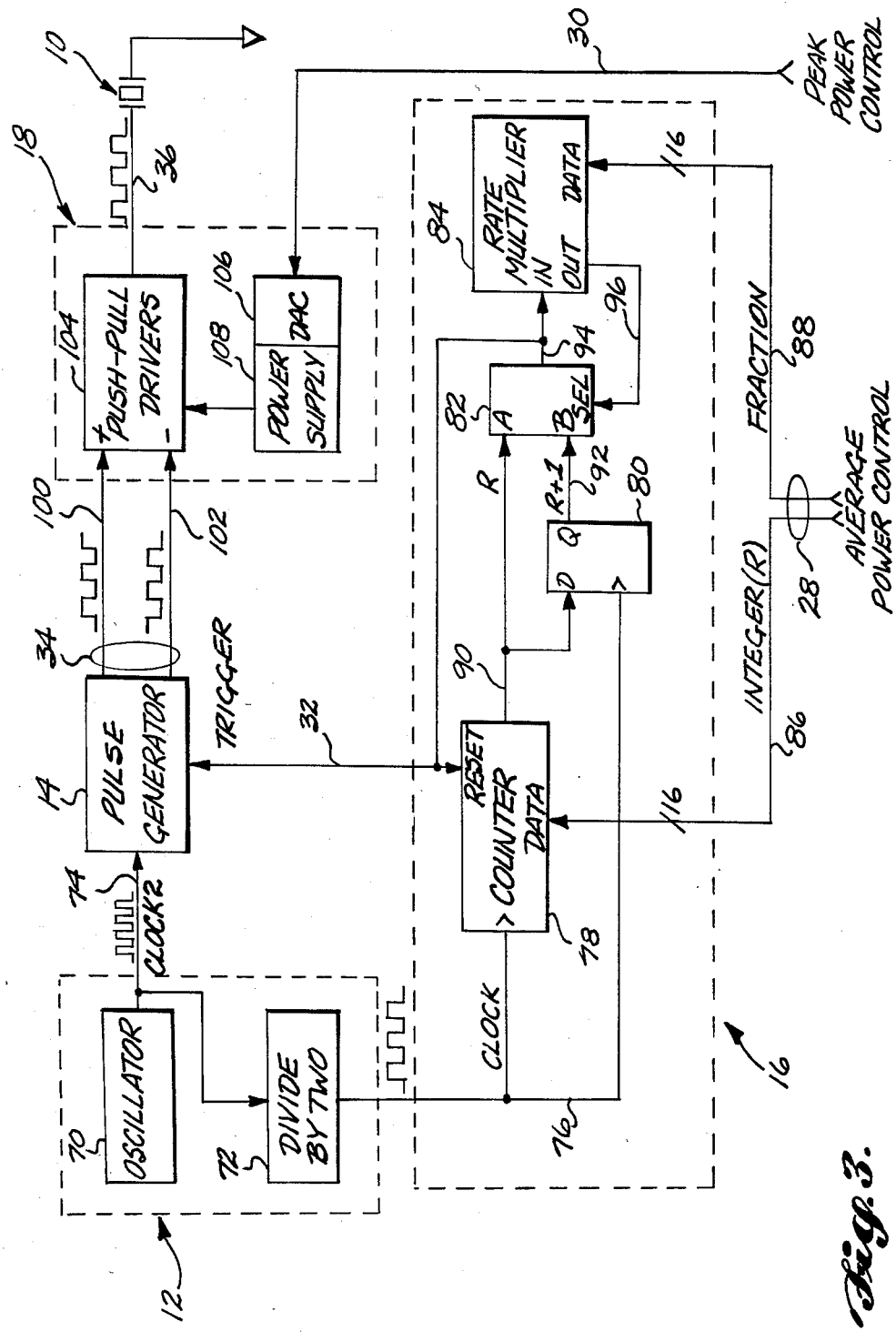
FIG. 3 is a circuit diagram of the apparatus of FIG. 1.

Int [ ] and Fr [ ] stand for the integer and fractional parts respectively of the bracketed expression, i.e., R is the largest integer less than or equal to W/D, and F is less than one. FIG. 3 sets forth a circuit diagram of one preferred apparatus adapted to implement the approach of equation (9). In the embodiment of FIG. 3, clock 12 comprises oscillator 70 and divide-by-two circuit 72.

Oscillator 70 produces a CLOCK2 signal at twice the frequency desired for drive pulses 40. The CLOCK2 signal is input to pulse generator 14 via line 74, and is also input into divide-by-two circuit 72. The divide-by-two circuit produces a CLOCK signal on line 76 that has a frequency corresponding to the desired drive pulse frequency. The CLOCK signal is input to timing circuit 16 that comprises counter 78, flip flop 80, data selector 82 and rate multiplier 84. The CLOCK signal is connected to the clock inputs of counter 78 and flip flop 80. As indicated in FIG. 3, the AVERAGE POWER CONTROL signal comprises a 16 bit INTEGER signal that is connected via data path 86 to the data input of counter 78, and a 6 bit FRACTION signal that is connected via data path 88 to the data input of rate multiplier 84. Referring to equation (9) above, the INTEGER signal on line 86 is a binary representation of the integer R. As explained below, the FRACTION signal on line 88 is proportional to F.

The operation of timing circuit 16 of FIG. 3 can be understood by assuming that a trigger pulse 44 has just been sent to pulse generator 14 over line 32. The trigger pulse is connected to the reset input of counter 78. The leading edge of the trigger pulse therefore loads the 16 bit INTEGER signal (R) supplied by the control circuit over line 86. Counter 78 then commences to count down from R to zero at a rate determined by the CLOCK signal on line 76. When R clock cycles of the CLOCK signal have occurred, counter 78 issues a high first timing signal on line 90 that is input to the A input of data selector 82 and into the D input of flip flop 80. Because of the delay inherent in counter 78, the first timing signal on line 90 does not reach the D input of flip flop 80 until after the beginning of the clock cycle that caused counter 78 to reach a count of zero. Flip flop 80 therefore produces a second timing signal on line 92 that is retarded by one clock cycle with respect to the first timing signal on line 90. The second timing signal on line 92 is connected to the B input of data selector 82. Data selector 82 connects either its A or its B input to its output on line 94, depending on the signal at its select (SEL) input. Thus, a high signal will appear on line 94 either R or R+1 clock cycles after the occurrence of a trigger pulse, the selection between R and R+1 being controlled by the signal on line 96.

The high signal on line 94 is coupled back to the RESET input of counter 78, where it causes the counter to pull line 90 low and to begin again counting down from R. As a result of line 90 going low, line 94 goes low either immediately (when input A is selected) or one clock cycle later (when input B is selected). Line 94 is connected to line 32, and the rising and falling signal on line 32 comprises the trigger pulses input to pulse generator 14.

The 6 bit FRACTION signal sent to rate multiplier 84 from the control circuit represents the fractional part F of the average number of clock cycles of wait time required to produce the selected duty cycle and average power levels. Rate multiplier 84 is a 6 bit device that produces 0-63 output pulses at its OUT terminal for every 64 input pulses appearing at its IN terminal, the number of output pulses per 64 input pulses depending upon the magnitude of the 6 bit binary signal applied to the DATA terminal. The IN terminal of the rate multiplier is connected to line 94, the OUT terminal is connected to line 96, and the DATA terminal is connected to data path 88. Control circuit 20 (FIG. 1) rounds the number W (equation (9)) to the nearest even multiple of 1/64, calculates R and F, and then sets the 6 bit FRACTION signal on data path 88 equal to F·64. As a result, for every 64 trigger pulses occurring on line 32, 64 pulses will be input to rate multiplier 84, and F·64 output pulses will be produced on line 96. Each time an output pulse is produced on line 96, input B of data selector 82 will be selected, and a wait time of R+1 clock cycles will be used. By such means, the relative frequency of use of R and R+1 clock cycle wait times will be adjusted, based upon the fraction F, to produce an average wait time W equal to R+F, in accordance with equation (9).

Still referring to FIG. 3, the standard pulses produced by pulse generator 14 in response to each trigger pulse are comprised of a first standard pulse signal on line 100 having a form similar to the signal of FIG. 2A, and a complementary second standard pulse signal on line 102. Variable gain amplifier 18 comprises push-pull drivers 104, power supply 108 and digital-to-analog converter (DAC) 106. DAC 106 converts the digital PEAK POWER CONTROL signal on line 30 to a corresponding analog signal, and power supply 108 boosts the power of such analog signal, and supplies it to conventional push-pull drivers 104 using a conventional class D amplification technique. The input to push-pull drivers 104 is the pair of complementary standard pulse signals on lines 100 and 102.

Figure 4:
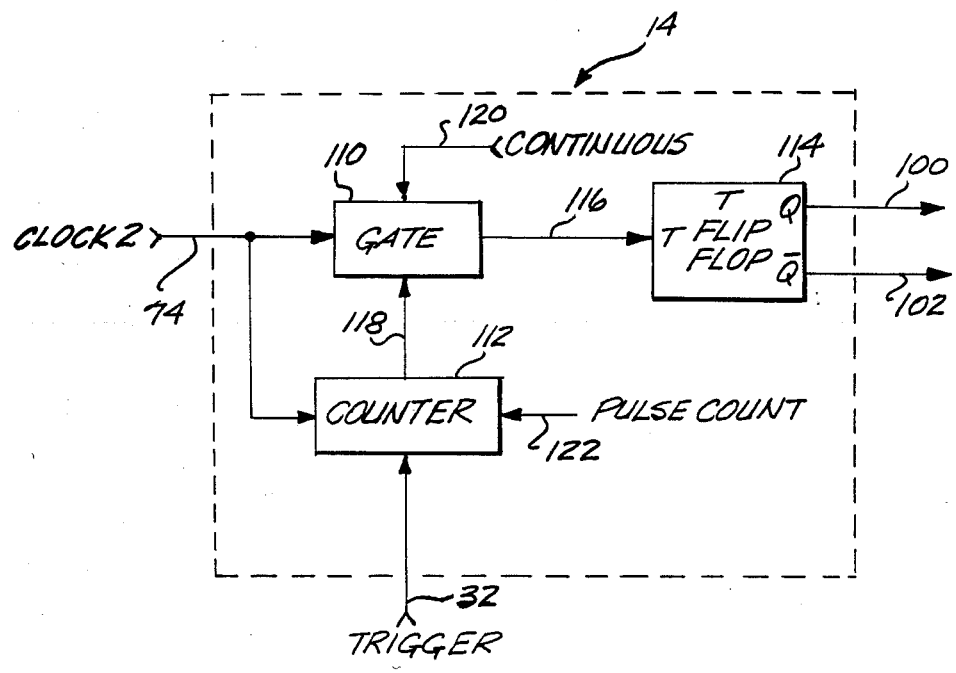
FIG. 4 is a circuit diagram of the pulse generator of FIG. 3.

A preferred embodiment of pulse generator 14 is set forth in FIG. 4. The pulse generator of this embodiment comprises gate 110, counter 112 and T flip flop 114. The CLOCK2 signal on line 74 is input to gate 110 and to counter 112. In response to a trigger pulse on line 32, counter 112 loads a predetermined PULSE COUNT signal from data path 122, and begins counting down from the number specified by the PULSE COUNT signal to zero at a rate controlled by the CLOCK2 signal. During the counting, counter 112 holds gate 110 open, such that the gate transfers the CLOCK2 signal to the T input of T flip flop 114 via line 116. The T flip flop responds by producing complementary standard pulse signals on lines 100 and 102, the frequency of the standard pulse signals being half of the frequency of the CLOCK2 signal. The number of cycles of the standard pulse signals produced on lines 100 and 102 in response to each trigger pulse therefore corresponds to the number specified by the PULSE COUNT signal. The individual lines comprising data path 122 may be connected directly to high and low voltage sources to produce a fixed number of standard and drive pulses per trigger pulse, or they may be connected via switches to permit easy modification of the PULSE COUNT signal. In another embodiment, the PULSE COUNT signal may be provided by control circuit 20 (FIG. 1).

It is sometimes convenient, for example during calibration procedures, to supply a continuous train of drive pulses to transducer 10. In such a case, an appropriate CONTINUOUS signal may be provided to pulse generator 14 via line 120. The CONTINUOUS signal causes gate 110 to be open regardless of the signal provided by counter 112 on line 118, thus providing continuous standard pulse signals on lines 100 and 102.

While the preferred embodiments of the invention have been illustrated and described, it should be understood that variations will be apparent to those skilled in the art. Accordingly, the invention is not to be limited to the specific embodiments illustrated and described, and the true scope and spirit of the invention are to be determined by reference to the following claims.

The embodiments of the invention in which an exclusive property or privilege is claimed are as follows:

1. An apparatus for generating acoustic radiation of selected peak and average power levels, the apparatus comprising an acoustic transducer and drive means for providing a drive signal to the acoustic transducer, the drive signal comprising a series of drive pulses, the drive means comprising:

means for establishing a series of fixed length clock cycles;

means for generating a series of trigger signals such that each trigger signal occurs either R or S clock cycles after the preceding trigger signal, R and S being positive integers;

pulse generating means responsive to each trigger signal to produce a selected number of standard pulses;

amplifier means for generating a drive pulse in response to each standard pulse, the amplitude of each drive pulse being adjusted such that the peak power of the acoustic radiation is equal to the selected peak power level; and control means for determining R and S such that the average power of the acoustic radiation is approximately equal to the selected average power level at the selected peak power level.

2. The apparatus of claim 1, wherein the means for generating a series of trigger signals comprises counting means for generating a first timing signal R clock cycles after the preceding trigger signal and a second timing signal S clock cycles after the preceding trigger signal, and selection means for selecting either the first or second timing signal and for producing the next trigger signal in response to the selected timing signal.

3. The apparatus of claims 1 or 2, wherein the number S is equal to R+1.

4. The apparatus of claim 3, wherein the control means comprises means for determining the average number of clock cycles between trigger signals required to produce acoustic radiation having the selected average power level at the selected peak power level, means for producing an INTEGER signal representative of the greatest integer less than or equal to said average number of clock cycles, and means for producing a FRACTION signal representative of the fractional portion of said average number of clock cycles.

5. The apparatus of claim 4, wherein the selection means is responsive to the FRACTION signal to select the second timing signal a fraction of times equal to the fractional portion of said average number of clock cycles.

6. The apparatus of claim 5, wherein the selection means comprises a bit rate multiplier.

7. The apparatus of claim 6, wherein the counting means comprises a counter adapted to load the INTEGER signal and to then produce the first timing signal after R clock cycles have elapsed, and delay means responsive to the first timing signal for producing the second timing signal, one clock cycle after the first timing signal.

8. The apparatus of claim 1, wherein the control means is adapted to produce a PEAK POWER CONTROL signal corresponding to the selected peak power level, and wherein the amplifier means amplifies each standard pulse to produce a corresponding drive pulse, the gain provided by the amplifier means being determined based upon the PEAK POWER CONTROL signal.

9. The apparatus of claim 8, wherein the gain provided by the amplifier means is proportional to a polynomial in $P_o$, wherein $P_o$ is the selected peak power level.

* * * * *